United States Patent
Lotz et al.

(10) Patent No.: US 9,809,519 B1
(45) Date of Patent: Nov. 7, 2017

(54) OXYGENATE SYNTHESIS AND HOMOLOGATION

(71) Applicant: ExxonMobil Chemical Patents Inc., Baytown, TX (US)

(72) Inventors: Monica D. Lotz, Houston, TX (US); Paul F. Keusenkothen, Houston, TX (US); Michael Salciccioli, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/497,705

(22) Filed: Apr. 26, 2017

Related U.S. Application Data

(60) Provisional application No. 62/342,016, filed on May 26, 2016.

(30) Foreign Application Priority Data

Aug. 5, 2016 (EP) .................................... 16182917

(51) Int. Cl.
| | | |
|---|---|---|
| C07C 29/158 | (2006.01) | |
| C07C 31/04 | (2006.01) | |
| C07C 31/08 | (2006.01) | |
| C07C 29/157 | (2006.01) | |
| C07C 31/12 | (2006.01) | |
| C07C 31/10 | (2006.01) | |
| C07C 29/32 | (2006.01) | |

(52) U.S. Cl.
CPC .......... *C07C 29/158* (2013.01); *C07C 29/157* (2013.01); *C07C 29/32* (2013.01); *C07C 31/04* (2013.01); *C07C 31/08* (2013.01); *C07C 31/10* (2013.01); *C07C 31/12* (2013.01)

(58) Field of Classification Search
CPC ..... C07C 29/157; C07C 29/158; C07C 29/32; C07C 31/04; C07C 31/08; C07C 31/10; C07C 31/12
See application file for complete search history.

(56) References Cited

U.S. PATENT DOCUMENTS

| | | |
|---|---|---|
| 3,911,041 A | 10/1975 | Kaeding et al. |
| 4,049,573 A | 9/1977 | Kaeding |
| 4,062,905 A | 12/1977 | Chang et al. |
| 4,079,095 A | 3/1978 | Givens et al. |
| 4,079,096 A | 3/1978 | Givens et al. |
| 4,122,110 A | 10/1978 | Sugier et al. |
| 4,265,828 A | 5/1981 | Knifton |
| 4,291,126 A | 9/1981 | Sugier et al. |
| 4,346,179 A | 8/1982 | Sugier et al. |
| 4,404,414 A | 9/1983 | Penick et al. |
| 4,499,327 A | 2/1985 | Kaiser |
| 4,605,677 A | 8/1986 | Knifton |
| 4,622,343 A | 11/1986 | Knifton et al. |
| 4,665,249 A | 5/1987 | Mao et al. |
| 4,935,547 A | 6/1990 | Leung et al. |
| 6,166,282 A | 12/2000 | Miller |
| 6,518,475 B2 | 2/2003 | Fung et al. |
| 7,083,762 B2 | 8/2006 | Kuechler et al. |
| 7,119,240 B2 | 10/2006 | Hall et al. |
| 7,227,048 B2 | 6/2007 | Chisholm et al. |
| 7,279,012 B2 | 10/2007 | Kuechler et al. |
| 7,781,633 B2 | 8/2010 | Vaughn et al. |
| 7,879,920 B2 | 2/2011 | Lattner et al. |
| 8,912,240 B2 | 12/2014 | Blank et al. |
| 2005/0107481 A1 | 5/2005 | Janssen et al. |
| 2007/0259972 A1 | 11/2007 | Lattner et al. |
| 2008/0033218 A1 | 2/2008 | Lattner et al. |
| 2015/0158785 A1 | 6/2015 | Soultanidis et al. |

FOREIGN PATENT DOCUMENTS

| | | |
|---|---|---|
| GB | 2 047 249 | 11/1980 |
| WO | 2012/050804 | 4/2012 |
| WO | 2012/078276 | 6/2012 |

OTHER PUBLICATIONS

Srinivas, et al., Prepr. Pap.-Am. Chem. Soc., Div. Energy Fuels 2013, vol. 58(2).

Jenner, "Novel Catalytic Procedure for Selective Homologation of Primary Alcohols", Journal of Molecular Catalysis, vol. 80 (1993), pp. L1-L4.

Pretzer et al, "Recent Advances in Alcohol Homologation: The Effect of Promoters", Catalytic Conversion of Synthesis Gas and Alcohols to Chemicals, R.G. Herman, Ed., Plenum Press, pp. 261-283 (1984).

Roper et al, "The Homologation of Methanol", Catalysis in C1 Chemistry, pp. 105-134, W. Keim, Ed., Reidel (1983).

Kiso et al, "Hydrogenation of Carbon Monoxide in the Presence of Homogeneous Ruthenium Catalysts: Effects of Onium Halides as Promoters", Journal of Organometallic Chemistry, vol. 312, pp. 357-364 (1986).

*Primary Examiner* — Jafar Parsa

(57) ABSTRACT

The invention relates to processes for oxygenate synthesis and homologation, to equipment and materials useful in such processes, and to the use of such oxygenate for producing olefin and polyolefin.

29 Claims, No Drawings

OXYGENATE SYNTHESIS AND HOMOLOGATION

PRIORITY

This invention claims priority to and the benefit of U.S. Patent Application Ser. No. 62/342,016, filed May 26, 2016, and European Patent Application No. 16182917.1 filed Aug. 5, 2016, both of which are herein incorporated by reference.

FIELD

The invention relates to processes for oxygenate synthesis and homologation, to equipment and materials useful in such processes, and to the use of such oxygenate for producing olefin and polyolefin.

BACKGROUND

Although methane is abundant, its relative inertness has limited its utility in conversion processes for producing higher-value hydrocarbons. For example, oxidative coupling methods generally involve highly exothermic and potentially hazardous methane combustion reactions, and frequently require expensive oxygen generation facilities and produce large quantities of environmentally sensitive carbon oxides. Non-oxidative methane conversion is equilibrium-limited, and temperatures ≥about 800° C. are needed for methane conversions greater than a few percent.

One way to avoid this difficulty involves converting methane to a mixture comprising carbon monoxide and molecular hydrogen (the mixture being conventionally referred to as "syngas"), converting the syngas to a mixture of oxygenates, and then converting the oxygenates to olefins. See, e.g., U.S. Patent Application Publication Nos. 2005/0107481 A1, 2008/0033218 A1, and 2007/0259972 A1, which disclose aspects of converting syngas to a mixture comprising methanol and ethanol, and then converting the mixture to a product mixture comprising ethylene and propylene. The mixture's methanol, in contrast, produces (i) ethylene and propylene, in approximately equal amounts, and (ii) a significant amount of by-products. Besides the desired methanol and ethanol, the process also yields relatively low-value by-products such as molecular hydrogen, water, carboxylic acids, ethers, carbon oxides, ammonia and other nitrogenated compounds, arsines, phosphines, and chlorides. Relatively low-value hydrocarbon by-products are also produced, such as acetylene, methyl acetylene, propadiene, butadiene, butylene, and the like. It is desired to decrease by-product yield, particularly hydrocarbon by-product yield, and increase oxygenate yield, particularly $C_{2+}$ alcohol yield, and more particularly $C_{3+}$ alcohol yield.

Conventional processes for increasing $C_{2+}$ alcohol selectivity include those disclosed in P.C.T. Patent Application Publication No. WO 2012/078276 A1. The reference discloses a heterogeneous catalytic process for producing ethanol and propanol from syngas. Although the reference's example report an ethanol selectivity of up to 22.4% and appreciable n-propanol selectivity (up to 7.6%), the process also produces a significant amount of methane (selectivity of up to about 13.8%). Homogeneous processes, such as those disclosed in U.S. Pat. Nos. 4,265,828; 4,605,677; and 8,912,240 have an increased selectivity for oxygenated products in comparison with the heterogeneous processes. Although methane yield is decreased, representative homogeneous processes, such as those disclosed in U.S. Pat. No. 4,622,343, exhibit appreciable methanol yield in comparison to their yield of more desirable ethanol. The amount of ethanol can be increased by homologation of recycled methanol, as disclosed in G. Srinavis, J. Martin, S. C. Gebhard, and M. V. Mundschau, Prepr. Pap.-Am. Chem. Soc. Div. Energy Fuels 2013, 58 (2). Similarly, U.S. Pat. No. 4,935,547 discloses recycling methanol or higher alcohols for homologation to produce higher boiling alcohols. It is also conventional to add gaseous alcohol to the gaseous syngas feed when producing ethyelene glycol (U.S. Pat. No. 4,265,828) or $C_1$-$C_4$ alcohol (U.S. Pat. No. 4,622,343).

Flexible processes are now desired, which can produce $C_{2+}$ oxygenates over a wide range of relative amounts, but with a lesser methane yield than conventional heterogeneous alcohol synthesis processes and a lesser methanol yield than conventional homogeneous alcohol synthesis processes. More particularly, processes are desired which have an increased yield of $C_{3+}$ alcohol over conventional processes, and which also make useful by-products such as $C_{2+}$ glycol.

SUMMARY

Certain aspects of the invention are based on the discovery that in homogeneous catalytic alcohol synthesis and/or homologation process it is beneficial to recycle a liquid-phase portion of the ethanol produced by the process. It has been found that introducing the recycled ethanol into the process in the liquid phase results in an increased yield of $C_{3+}$ monohydric alcohol and an increased yield of $C_{2+}$ glycol. It was expected that recycling liquid-phase ethanol would cause an undesirable increase in methanol yield, mainly as a result of the hydrogenolysis of acetic acid and methyl acetate intermediates. Instead, it has surprisingly been found that reintroducing a portion of the ethanol product into the reaction in the liquid phase in the presence of carbon monoxide, molecular hydrogen and a catalytically active material increases $C_{3+}$ monohydric alcohol yield and $C_{2+}$ glycol yield for a broad range of feeds, process conditions, and active materials. Reintroducing a portion of the ethanol product into the reaction in the liquid phase has also been found to decrease the yield of methanol compared to convention processes which do not recycle ethanol in the liquid phase. While not wishing to be bound by any theory or model, it is believed that recycling ethanol in the liquid phase provides a kinetic advantage to oxygenate homologation reactions by more readily enabling oxygenate coordination with the catalytic sites of the active material, resulting in more efficient carboxylation and hydrogenation.

Accordingly, certain aspects of the invention relate to a process for producing oxygenate from a feed mixture comprising molecular hydrogen and >0.01 wt. % of carbon monoxide. A process fluid is provided which includes at least one active material, the active material comprising a metal-containing compound which includes at least one of Co, Rh, Pd, Pt, Ni, Os, Ir, Cr, Mn, Fe, Re, and Ru. A reaction mixture is produced by reacting at least a portion of the feed mixture's CO and at least a portion of the feed mixture's molecular hydrogen in the presence of the process fluid under oxygenate formation conditions. The reaction mixture comprises oxygenate produced by the reaction, un-reacted feed mixture, and typically at least a portion of the process fluid. The oxygenate comprises $C_{2+}$ glycol, ethanol, and $C_{3+}$ monohydric alcohol. The process also includes separating from the reaction mixture (i) at least a portion of the ethanol, (ii) at least a portion of the $C_{3+}$ monohydric alcohol, and (iii) at least a portion of the $C_{2+}$ glycol. A liquid-phase portion of the separated ethanol is recycled to the reaction, and at least a portion of the separated $C_{3+}$ monohydric alcohol is conducted away. At least a portion of the separated $C_{2+}$ glycol is also conducted away.

It is believed non-ethanol $C_{2+}$ oxygenate beneficially acts as a co-solvent which enhances the solubility of oxygenated and/or carbonylated intermediates. Recycling non-ethanol $C_{2+}$ oxygenate, particularly $C_2$ oxygenate such as ethylene glycol is therefore believed to prevent precipitation of oxygenated and/or carbonylated intermediates during the homogeneous catalytic oxygenate formation reaction. Maintaining these intermediates in the liquid phase during homologation further increases the processes' yield of $C_{3+}$ monohydric alcohol and $C_{2+}$ glycol. Reintroducing a portion of the non-ethanol $C_{2+}$ oxygenate product into the reaction in has also been found to decrease the yield of methanol compared to conventional processes which do not recycle non-ethanol $C_{2+}$ oxygenate. Accordingly, certain aspects of the invention relate to producing oxygenate from a feed mixture comprising molecular hydrogen, ≥0.01 wt. % of carbon monoxide. A process fluid is provided which includes organic oxygenate and at least one active material, the active material comprising a metal-containing compound which includes at least one of Co, Rh, Pd, Pt, Ni, Os, Ir, Cr, Mn, Fe, Re, and Ru. At least a portion of the feed mixture's CO and at least a portion of the feed mixture's molecular hydrogen are reacted in the presence of the process fluid under oxygenate formation conditions to produce ethanol, $C_{3+}$ monohydric alcohol, and non-ethanol $C_{2+}$ oxygenate. At least a portion of the non-alcohol $C_{2+}$ oxygenate, e.g., at least a portion of the non-ethanol $C_2$ oxygenate, is recycled to the oxygenate formation reaction. At least a portion of the $C_{3+}$ monohydric alcohol is conducted away.

DETAILED DESCRIPTION

Definitions

For the purpose of this description and appended claims, the following terms are defined:

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule, wherein n is a positive integer. The term "$C_{n-}$" hydrocarbon means hydrocarbon having no more than n number of carbon atom(s) per molecule, wherein n is a positive integer. The term "hydrocarbon" means a class of compounds containing hydrogen bound to carbon, and encompasses (i) saturated hydrocarbon, (ii) unsaturated hydrocarbon, and (iii) mixtures of hydrocarbons, including mixtures of hydrocarbon compounds (saturated and/or unsaturated), including mixtures of hydrocarbon compounds having different values of n.

The term "$C_n$ alcohol" means monohydric alcohol having n carbon atom(s) per molecule, wherein n is a positive integer. The term "$C_{n+}$ alcohol" means monohydric alcohol having at least n carbon atom(s) per molecule, wherein n is a positive integer. The term "$C_{n-}$ alcohol" means monohydric alcohol having no more than n number of carbon atom(s) per molecule, wherein n is a positive integer. The term "glycol" means multi-hydric alcohol, e.g., dihydric alcohol such as ethylene glycol (1,2 ethandiol) and propylene glycol (1,3 propandiol). "$C_n$ glycol" means glycol having n carbon atom(s) per molecule, wherein n is a positive integer. The term "$C_{n+}$ glycol" means glycol having at least n carbon atom(s) per molecule, wherein n is a positive integer. The term "$C_{n-}$ glycol" means glycol having no more than n number of carbon atom(s) per molecule, wherein n is a positive integer. The term alcohol encompasses (i) saturated and unsaturated alcohol compounds, (ii) primary, secondary, and tertiary alcohol compounds, (iii) alcohol compounds having a terminal hydroxyl group (1-alcohol) and alcohol compounds having a hydroxyl group in a non-terminal position (2-alcohol, 3-alcohol, etc.), and (iv) mixtures of two or more alcohol compounds, including mixtures of alcohol compounds having different values of n. The term glycol encompasses (i) saturated and unsaturated glycol compounds, (ii) glycol compounds which are one or more of primary, secondary, and tertiary, (iii) glycol compounds having at least one terminal hydroxyl group and glycol compounds having at least one hydroxyl group in a non-terminal position, and (iv) mixtures of two or more glycol compounds, including mixtures of glycol compounds having different values of n.

The terms "alkane" and "paraffinic hydrocarbon" mean substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes. Aliphatic hydrocarbon means hydrocarbon that is substantially free of hydrocarbon compounds having carbon atoms arranged in one or more rings.

The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond.

The term "Periodic Table" means the Periodic Chart of the Elements, as it appears on the inside cover of The Merck Index, Twelfth Edition, Merck & Co., Inc., 1996.

The term "reaction zone" or "reactor zone" mean a location within a reactor, e.g., a specific volume within a reactor, for carrying out a specified reaction. A reactor or reaction stage can encompass one or more reaction zones. More than one reaction can be carried out in a reactor, stage, or zone. For example, a reaction stage can include a first zone for carrying out first and second reactions and a second zone for carrying out a third reaction, where the first reaction (e.g., syngas generation) can be the same as or different from the second reaction (e.g., oxygenate formation) and the third reaction (e.g., alcohol dehydration).

When used in connection with a specified reactant, the term "conversion" means the amount of the reactant (weight basis) consumed in the reaction. For example, when the specified reactant is $C_3$ alcohol, 100% conversion means 100% of the $C_3$ alcohol is consumed in the reaction. The term "selectivity" refers to the production (weight basis) of a specified compound in a reaction. As an example, the phrase "a $C_3$ alcohol dehydration reaction has 100% selectivity for propylene" means that 100% of the $C_3$ alcohol (weight basis) that is converted in the dehydration reaction is converted to propylene. Yield (weight basis) is conversion times selectivity.

Certain aspects the invention relate to a process for catalytically producing $C_{3+}$ monohydric alcohol and optionally $C_{2+}$ glycol from a feed mixture comprising carbon monoxide and molecular hydrogen. Typical feed mixtures will now be described in more detail. The invention is not limited to these feed mixtures, and this description is not meant to foreclose the use of other feed mixtures within the broader scope of the invention.

Feed Mixture

The feed mixture comprises molecular hydrogen and carbon monoxide, e.g., ≥0.01 wt. % carbon monoxide based on the weight of the feed mixture, such as ≥1 wt. %, or ≥5 wt. %. A wide range of molecular hydrogen: carbon monoxide molar ratios can be used, e.g., in the range of from 0.01 to 10. The feed mixture typically comprises ≥5 wt. % carbon monoxide and optionally further comprises diluent such as carbon dioxide. For example, the feed mixture can comprise 50 wt. % to 99 wt. % of carbon monoxide, with ≥50 wt. % of the balance being molecular hydrogen. The feed mixture can have, e.g., a molecular hydrogen: carbon monoxide molar ratio in the range of from, e.g., 0.25 to 20, such as 0.5 to 20. Such mixtures are typically referred to as synthesis gas (or "syngas").

In certain aspects, the feed mixture includes syngas comprising molecular hydrogen, ≥10 wt. % carbon monoxide, and diluent. The diluent can comprise carbon dioxide, for example. The syngas typically has an $H_2$: $(CO+CO_2)$ molar ratio in the range of from 0.25 to 10, or 0.5 to 10, e.g., an $H_2$:CO ratio in the range of from 0.25 to 10, or 0.25 to 5, or 0.5 to 5. Certain suitable syngas mixtures have an $H_2$: CO molar ratio in the range of from 0.25 to 4, or 0.5 to 2. The syngas can be produced from a carbon-containing source material, such as hydrocarbon, e.g., hydrocarbon in the form of one or more of natural gas, petroleum, coal, biomass, including mixtures thereof, derivatives thereof, and mixtures of such derivatives. The type of carbon-containing source material used is not critical. The source material typically comprises ≥10 vol. % of at least one hydrocarbon, e.g., methane, such as ≥50 vol. %, based on the volume of the source material.

Any convenient method for producing syngas can be used, including conventional methods. Suitable methods include those described in U.S. Patent Application Publication Nos. 2007/0259972 A1; 2008/0033218 A1; and 2005/0107481, each of which is incorporated by reference herein in its entirety. For example, natural gas can be converted to syngas by steam reforming. Typically, the natural gas is treated before the steam reforming, e.g., to remove at least a portion of any inert components in the natural gas, such as nitrogen, argon, and carbon dioxide. The treated natural gas typically comprises methane, ethane, and can further comprise higher alkanes, such as propane. The natural gas can be associated natural gas, for example. One suitable natural gas comprises more than 90 vol. % methane.

During steam reforming, the natural gas feed contacts steam in the presence of a catalyst, such as one or more metals or compounds thereof selected from Groups 7 to 10 of the Periodic Table. The catalyst is typically supported on at least one attrition-resistant refractory support, such as alumina. The contacting is normally conducted at high temperature, such as in the range of from 800° C. to 1100° C., and pressures <5000 kPa. Under these conditions, methane converts to carbon monoxide and hydrogen according to reactions, such as:

$$CH_4 + H_2O \rightarrow CO + 3H_2.$$

Steam reforming is energy intensive, typically using at least 200 kJ/mole of methane consumed. Alternatively or in addition to steam reforming, syngas can be produced by partial oxidation of hydrocarbon. During partial oxidation, a hydrocarbon such as methane is burned in an oxygen-lean environment. The methane is partially-oxidized to carbon monoxide (reaction (i)), with a portion of the carbon monoxide being exposed to steam reforming conditions (reaction (ii)) to produce molecular hydrogen and carbon dioxide, according to the following representative reactions:

$$CH_4 + 3/2\ O_2 \rightarrow CO + 2H_2O \quad \text{(i) and}$$

$$CO + H_2O \rightarrow CO_2 + H_2 \quad \text{(ii).}$$

Partial oxidation is exothermic and yields a significant amount of heat. Because one reaction is endothermic and the other is exothermic, and because they can be configured to use substantially the same feed, steam reforming and partial oxidation are often performed together for efficient energy usage. Combining the steam reforming and partial oxidation yields a third process wherein the heat generated by the partial oxidation is used to drive the steam reforming to yield syngas. The syngas is reacted under oxygenation formation conditions in the presence of a process fluid which includes at least one active material. The active material comprises at least one metal-containing compound which includes at least one of Co, Rh, Pd, Pt, Os, Ir, Cr, Mn, Fe, Re, and Ru. Particular aspects of the process fluid and active material will now be described in more detail. The invention is not limited to these aspects, and this description is not meant to foreclose other process fluids and active materials within the broader scope of the invention.

Process Fluid and Catalyst

The oxygenate formation reaction is a homogeneous catalytic reaction carried out primarily in the liquid phase. The active material is typically in the form of a complex catalyst system having components which operate together in the process fluid to convert the feed's carbon monoxide and molecular hydrogen to a product comprising $C_{3+}$ monohydric alcohol and $C_{2+}$ glycol. The active material is typically dissolved, dispersed, suspended, or otherwise distributed in a carrier fluid to form a process fluid that is primarily in the liquid phase under reaction conditions. The homogeneous catalytic reaction (the oxygenate formation reaction) produces $C_{3+}$ monohydric alcohol and $C_{2+}$ glycol products that are also primarily in the liquid phase under the oxygenate formation conditions. A small amount of heterogeneous active material (or components thereof or precursors thereof) can be present in the active material, e.g., in an amount ≤1 wt. %, such as ≤0.1 wt. %, based on the weight of the process fluid. Typically, however, any heterogeneous active material will become dissolved, dispersed, suspended, or otherwise distributed in the process fluid during the oxygenate formation reaction, e.g., by reaction with molecular hydrogen, carbon monoxide, dispersed active material, and/or other components of the process fluid.

The active material includes at least one metal-containing compound, typically a metal complex which includes one or more of Co, Rh, Pd, Pt, Ni, Os, Ir, Cr, Mn, Fe, Re, and Ru, e.g., one or more of Co, Rh, Re, and Ru. For the purpose of this description and appended claims, when the active material includes a metal-containing compound having one only one of the specified metal atoms, the metal compound is represented by [M]. When the active material includes a metal-containing compound having two of the specified metal atoms (e.g., metal compounds which include di-cobalt or ruthenium bound to cobalt), the first metal-containing compound is by [M] and the second by [M']. Those skilled in the art will appreciate that the foregoing representation is a simplification. The invention is not limited to active materials conforming to this representation, and this description does not foreclose other active materials within the broader scope of the invention.

The process can be carried out using a wide variety of organic or inorganic compounds, complexes, etc. which contain one or more of the specified metals, although typically the active material can be readily dissolved, dispersed, suspended, or otherwise distributed in the process fluid, and will remain so under oxygenate formation conditions. Typically, the process fluid is formed by adding the active material and/or active material precursors to a carrier fluid, e.g., one or more molten onium salts. Typically, the onium salt is selected from among those, that are primarily in the liquid phase under the oxygenate formation conditions. Representative onium salts, e.g., onium halides, are disclosed in Novel Catalytic Procedure for Selective Homologation of Primary Alcohols, G. Jenner, Journal of Molecular Catalysis, 80 (1993) L1-L4, which is incorporated by reference herein in its entirety. Besides their utility as a homogeneous medium for carrying out the oxygenate formation reaction, onium salts favorably increase [M] stability during the reaction.

It is within the scope of the invention to add additional active material and/or active material precursor to the process fluid, e.g., before the process fluid is introduced into the reaction and/or afterward. It is also within the scope of the invention to remove active material, including components and precursors thereof, from the process fluid. This can be carried out, e.g., before the process fluid is introduced into the reaction and/or afterward.

The active material can be produced during the oxygenate formation reaction, e.g., from one or more precursors which have been added or recycled to a carrier fluid and/or the process fluid. The precursor typically contains a compound of the specified metal or metals in an ionic state. The active material and/or precursor thereof can be present in the process fluid in a variety of forms, e.g., in the form of metal on a carbonaceous support such as metal carbon, metal on an inorganic refractory support such as metal on alumina, organic metal complexes such as metal acetylacetonate, and inorganic metal compounds such as metal carbonyl. Functionalized derivatives of one or more of these active material precursors are also within the scope of the invention. While not wishing to be bound by any theory or model, it is believed that during oxygenate formation the active material comprises one or more of the specified metals in complex combination with carbon monoxide and/or hydrogen, e.g., in the form of a metal-containing compound where one or more of the specified metals is directly bonded to carbon monoxide (metal carbonyl form, including hydrocarbonyl derivatives thereof).

Conventional active material and active material precursors can be used, e.g., those described in U.S. Pat. Nos. 4,265,828; 4,605,677; 4,622,343; 4,935,547; and 8,912,240. In certain aspects, the active material comprises at least one compound which includes one or more of Ru, Co, and Rh. In certain aspects, one or more promoters are added to the process fluid and/or carrier fluid to increase the active material's effectiveness. For example, promoters which include halogen can be used, such as one or more of F, Cl, Br, I, and At; typically one or more of Cl, Br, and I; or Br and/or I. The halogen can be a coordinated halogen, e.g., when present in the active material the halogen is coordinated with one or more of the active material's metal, such as [Br M]. The invention also encompasses active material associated with non-coordinated halogen, including halogen present as a counterion, e.g., [M]$^+$ Br$^-$. Promoters which provide a relatively strong activation, e.g., $I_2$, $CH_3I$, and HI, and those which provide a more mild activation, e.g., NaI, LiI, KI, $CaI_2$, and $SrI_2$, are within the scope of the invention, as are non-halogen promoters such as cesium benzoate, $Na_2B_4O_7$, $HKCO_3$, and $(NH_4)_2HPO_4$. The catalyst system may optionally further include a chloride or bromide-containing compound as a promoter. One suitable class of promoters includes organic halide, e.g., hydrocarbyl halide, such as those having one or more hydrocarbyl groups of from 1 to 10 carbon atoms. Representative examples of this class of promoter include methyl chloride, butyl chloride, acetyl chloride, hydrogen chloride, cobalt chloride, as well as the corresponding bromide compounds. Other representative promoters include triorgano-onium salt of one or more Group 15 atoms, e.g., triorganophosphonium. Such promoters have the general formula [R1 R2 R3 Φ H] [Ψ]. R1, R2, and R3 are each independently selected from $C_1$-$C_{24}$ alkyl, aryl and alkaryl hydrocarbyl groups or functionalized alkyl, aryl and alkaryl groups. For example, such groups can contain one or more of ether, alcohol, ketone, carboxylic acid or ester, amine, amide, thioether, phosphine oxide, nitrile, heteroaromatic, or fluorocarbon groups. Φ is selected from Group 15 of the Periodic Table, e.g., P, As, Sb, and Bi. Ψ is a halogen counterion, e.g., chloride, bromide, or iodide. Examples of suitable triorganophosphonium salts include tributylphosphonium chloride, triphenylphosphonium chloride, tributylphosphonium bromide, and triphenylphosphonium bromide, such as trialkylphosphonium salts containing alkyl groups having 1-6 carbon atoms, including methyl, ethyl, and butyl. Suitable promoters are disclosed in (i) U.S. Pat. No. 8,912,240; (ii) Recent Advances in Alcohol Homologation: The Effect of Promoters, W. R. Pretzer and M. M. Habib, in Catalytic Conversion of Synthesis Gas and Alcohols to Chemicals, 261-283, R. G. Herman, Ed., Plenum (1984); and (iii) The Homologation of Methanol, M. Röper and H. Lovenich, in Catalysis in $C_1$ Chemistry 105-134, W. Keim, Ed., Reidel (1983), each of which is incorporated by reference herein in its entirety. When used, the promoter: [M] molar ratio is typically in the range of 0.05:1 to 3.5:1 during the oxygenate formation reaction, e.g., 0.05:1 to 3:1, or 0.1:1 to 2.5:1, or 0.05:1 to 1:1, or 0.1:1 to 0.9:1, or 0.2:1 to 0.8:1. When the promoter includes triorganophosphonium salt, the triorganophosphonium salt to [M] molar ratio is typically in the range of 0.2:1 to 0.6:1.

Typically, [M] has the form of a metal complex which contains carbon monoxide directly bonded to one or more of the specified metals, e.g., ruthenium carbonyl. Although it is within the scope of the invention to do so, typically the compound or compounds of the specified metals provided to the reaction are not in a form (e.g., chemical state) which will effectively catalyze the desired oxygenate formation reaction. Even metal compounds containing one or more bound carbon monoxide ligands may undergo a change in form, chemical state, or composition which initiates or improves its activity for catalyzing the desired reaction. Compounds which include one or more of the specified metals can be introduced into the reaction directly and/or by adding them to the carrier fluid and/or process fluid before introducing the process fluid into the reaction. For example, compounds of one or more of the specified metals can be added to a carrier fluid and/or the process fluid as salts, oxides and carbonyl clusters, which become solubilized, dispersed, suspended, or otherwise distributed in the process fluid, and which are converted under the reaction's oxygenate formation conditions to a form which effectively catalyzes the reaction, e.g., [M] (CO). Typically, at least a portion of the process fluid is produced at the start of the process by adding one or more metal-containing precursors of the active material to a carrier fluid comprising at least one molten onium salt, and then exposing the combined carrier fluid+precursor mixture to oxygenate formation conditions in the presence of carbon monoxide and molecular hydrogen. If desired, additional active material or active material precursor can be added to the process fluid at any convenient location in the process.

Certain aspects of the invention will now be described in more detail with respect to active materials containing ruthenium and/or cobalt. The invention is not limited to these aspects, and this description is not meant to foreclose other active materials encompassed by the broader scope of the invention, such as those containing rhodium, manganese, etc. For example, the active material can be one that includes ≤0.1 wt. % Ru, e.g., ≤0.01 wt. %, or is substantially free of Ru.

For active material which include ruthenium, the active material is typically produced during the oxygenate formation reaction from one or more ruthenium-containing precursors. The form of ruthenium-containing precursor is not critical, and more than one form can be used. For example, a ruthenium-containing precursor can be introduced into the process fluid and/or carrier fluid in oxide form, e.g., one or more of ruthenium(IV) oxide hydrate, anhydrous ruthenium (IV) dioxide and ruthenium(VIII) tetraoxide. Alternatively or in addition, a ruthenium-containing precursor can be introduced into the process fluid and/or carrier fluid as the salt of a mineral acid, e.g., ruthenium(III) chloride hydrate, ruthenium(III) bromide, ruthenium(III) triiodide, tricarbonyl ruthenium(II)iodide, anhydrous ruthenium(III) chloride and ruthenium nitrate, and/or as the salt of an organic carboxylic acid such as one or more of ruthenium(III) acetate napthth- enate, ruthenium valerate and ruthenium(III) acetylacetonate. The ruthenium-containing precursor may also be added to the process fluid and/or carrier fluid as one or more of carbonyl, hydrocarbonyl, substituted carbonyl, and substituted hydrocarbonyl; e.g., one or more of triruthenium dodecacarbonyl, $H_2 Ru_4 (CO)_{13}$ and $H_4 Ru_4 (CO)_{12}$, tricarbonylruthenium(II) chloride dimer, $[Ru(CO)_3 Cl_2]_2$.

Alternatively or in addition to ruthenium, the active material and/or its precursor can include cobalt. As in the case of active materials which include ruthenium, one or more cobalt-containing active materials can be produced during the oxygenate formation reaction from one or more cobalt-containing precursors. The form of cobalt-containing precursor is not critical, and more than one form can be used. For example, a cobalt-containing precursor can be introduced into the process fluid and/or carrier fluid in oxide form, e.g., as one or more of cobalt(II) oxide (CoO) or cobalt(II,III) oxide ($Co_3 O_4$). Other suitable forms of cobalt include one or more of (i) one or more salts of mineral acid, such as cobalt(II) nitrate, hydrate ($Co(NO_3)_2$ $6H_2 O$), cobalt (II) sulphate, etc.; (ii) one or more salt of organic carboxylic acid, such as cobalt(II) formate, cobalt(II) acetate, cobalt(II) propionate, cobalt(II) oxalate, cobalt naphthenate; (iii) one or more carbide, such as cobalt carbide; (iv) one or more carbonate, such as cobalt(II) carbonate; and (v) one or more of carbonyl, hydrocarbonyl, and substituted carbonyl of cobalt, including complexes with carbonyl-containing ligands, such as cobalt(II) acetylacetonate and cobalt(III) acetylacetonates, etc. Suitable carbonyl, hydrocarbonyl, and substituted hydrocarbonyl include dicobalt octacarbonyl ($Co_2 (CO)_8$), cobalt hydrocarbonyl ($HCo(CO)_4$) and triphenyl phosphine cobalt tricarbonyl dimer, etc.

As is the case with the foregoing cobalt and ruthenium compounds, active material comprising the desired compounds (or precursors) of the other specified metals can be introduced into the oxygenate formation reaction by way of one or more of (i) direct introduction into the reaction, (ii), introduction via the carrier fluid, and (iii) introduction via the process fluid. Certain suspects of the invention will now be described in more detail, which include introducing into a carrier fluid one or more of (i) fresh active material, (ii) components thereof, (iii) precursors thereof, (iv) regenerated active material, (v) regenerated components thereof, and (vi) regenerated precursors thereof. The invention is not limited to these aspects, and this description is not meant to foreclose other aspects within the broader scope of the invention, such as those which utilize a different form of carrier fluid and those which include introducing active material, regenerated active material, components, precursors, etc. directly into the oxygenate formation reaction and/or via the process fluid.

In certain aspects at least a portion of the metal-containing compound of the active material or components thereof or precursors thereof is dispersed in a carrier fluid that is primarily liquid-phase, and which remains so under the oxygenate formation conditions. The oxygenate formation conditions include (i) a reaction pressure within a reaction pressure range and (ii) a reaction temperature within a reaction temperature range. The carrier fluid typically has (i) a melting point at the reaction pressure that is less than the reaction temperature and (ii) a boiling point at the reaction pressure that is greater than the reaction temperature. Suitable carrier fluids include one or more tetraorgano onium salts of atoms selected from Group 15 of the Periodic Table, e.g., those having general formula [R1 R2 R3 R4 Φ] [Ψ]. R1, R2, R3, and R4 are each independently selected from $C_1$-$C_{24}$ alkyl, aryl and alkaryl hydrocarbyl groups or functionalized alkyl, aryl and alkaryl groups. For example, such groups can contain one or more of ether, alcohol, ketone, carboxylic acid or ester, amine, amide, thioether, phosphine oxide, nitrile, heteroaromatic, or fluorocarbon groups. Φ is selected from Group 15 of the Periodic Table, e.g., P, As, Sb, and Bi. Ψ is a halogen counterion such as chloride, bromide, or iodide. Examples of suitable tetraorganophosphonium salts include tetrabutylphosphonium chloride, heptyltriphenylphosphonium chloride, tetrabutylphosphonium bromide, and heptyltriphenylphosphonium bromide. Typically, the tetraorganophosphonium salt includes one or more tetraalkylphosphonium salt containing at least one alkyl groups having from 1-6 carbon atoms, such as methyl, ethyl, and butyl, e.g., tetrabutylphosphonium salt. The tetrabutylphosphonium salt can be tetrabutylphosphonium chloride, for example. Tetraorgano onium salts that are suitable for use as carrier fluid are described in U.S. Pat. Nos. 4,265,828; 4,605,677; 4,622,343; 4,935,547; and 8,912,240. Typically, sufficient active material or active material precursor is added to the carrier fluid so that the amount of active material in the resulting process fluid is ≥0.01 wt. % based on the weight of the process fluid, e.g., in the range of from about 0.01 wt. % to about 30 wt. %, such as from about 1 wt. % to about 25 wt. %. For active materials which contain one or more of Co, Rh, Pd, Pt, Ni, Os, Ir, Cr, Mn, Fe, Re, and Ru, these are typically present (alone or in combination) in the process fluid in an amount ≥0.2 wt. %, e.g., in the range of from 0.2 wt. % to 10 wt. %, such as from about 0.5 wt. % to 5 wt. %.

Although the carrier fluid and/or process fluid can further comprise a solvent, e.g., added methanol, typically a solvent is not used. When methanol is present in the process fluid, e.g., as added methanol and/or methanol produced in the oxygenate formation reaction, it is typical for the methanol amount to be in the range of from 0.01 moles of methanol per liter of process fluid to 10 moles of methanol per liter of process fluid, e.g., 0.1 moles/liter to 5 moles/liter, such as 0.5 moles/liter to 2 moles/liter. Those skilled in the art will appreciate that even though using one or more solvents can increase the effectiveness of certain carrier fluids, e.g., onium chlorides, the solvent's participation in the oxygenate formation reaction can lead to undesired side reactions, e.g., solvent decomposition, resulting in an increased difficulty in recovering the desired $C_{3+}$ monohydric alcohol and $C_{2+}$ glycol products. Optional solvents include those disclosed in the Jenner article and those disclosed in Hydrogenation of Carbon Monoxide in the Presence of Homogeneous Ruthenium Catalysts: Effects of Onium Halides as Promoters, Y. Kiso, et al., Journal of Organometallic Chemistry, 312 (1986) 357-364. Other suitable solvents include those disclosed in the Röper article.

Aspects of the homogeneous oxygenate formation reaction will now be described in more detail with reference to producing $C_{3+}$ monohydric alcohol and $C_{2+}$ glycol from syngas using an active material which includes $Co_2(CO)_8$, the active material being dispersed in a primarily liquid phase carrier fluid which includes tetrabutylphosphonium bromide. The invention is not limited to these aspects, and this description is not meant to foreclose other aspects within the broader scope of the invention such as those where the active material includes Ru instead of or in addition to Co, and those which utilize a different carrier fluid or do not use a carrier fluid.

Oxygenate Formation

In certain aspects, the desired $C_{3+}$ monohydric alcohol and $C_{2+}$ glycol are produced by first synthesizing aldehyde, such as $H_2CO$. Alcohol and glycol are produced from the aldehyde by catalytic CO insertion and catalytic hydrogen insertion. $C_{2+}$ monohydric alcohol and $C_{2+}$ glycol are produced from methanol and ethanol, primarily by homologation. When using the specified $Co_2(CO)_8$ active material (or precursor thereof), represented by [M][M'], it is believed that the oxygenate formation reactions proceed in the presence of syngas under oxygenate formation conditions according to the following pathways.

First, active material is formed from active material precursors by reactions $$H_2+[M][M']\rightarrow H[M]+H[M'] \text{ and} \qquad (1)$$

$$2\{H[M]\}+2(CO)\rightarrow 2\{[M]CO\}+H_2. \qquad (2)$$

The active material is reacted with syngas to produce aldehyde, by way of $$CO+H[M]\rightarrow [M]HCO, \text{ which then reacts as} \qquad (3)$$

$$[M]HCO+H[M']\rightarrow H_2CO+[M][M']. \qquad (4)$$

Additional active material is formed from molecular hydrogen in the syngas according to equation (1), which continues the reaction.

Methanol (and/or additional methanol, when methanol is included in the carrier fluid) is believed to be produced according to the flowing pathway.

$$H_2CO+H[M]+H[M']\rightarrow CH_3OH+[M][M']. \qquad (5)$$

Additional active material is formed from molecular hydrogen in the syngas according to equation (1), which continues the reaction.

Ethylene glycol is believed to be produced according to the following pathway, $$H_2CO+[M]CO+H[M']\rightarrow H_2CO[M]CO[M']H, \text{ which then reacts via} \qquad (6)$$

$$H_2CO[M]CO[M']H\rightarrow OCH_2COH+[M][M'], \text{ which after repeating equation (1) twice leads to both:} \qquad (7)$$

$$OCH_2COH+H[M']+H[M]\rightarrow HOCH_2CH_2O+[M][M'], \text{ and} \qquad (8)$$

$$2\{HOCH_2CH_2O\}+H[M']+H[M]\rightarrow 2\{HOCH_2CH_2OH\}+[M][M']. \qquad (9)$$

A continuous oxygenate formation process can be carried out by repeating reactions (1)-(9), and carrying out the desired amount of homologation.

The methanol produced in reaction (5) is typically retained in the oxygenate formation reaction zone (or recycled to it) for homologation to ethanol $C_{3+}$ monohydric alcohol. The ethylene glycol ($HOCH_2CH_2OH$) produced in reaction (9) can be separated and conducted away. Alternatively, at least a portion of the ethylene glycol can be retained in the oxygenate formation reaction zone and/or recycled to it for homologation to $C_{3+}$ glycol. Those skilled in the art will appreciate that the relative amounts of molecular hydrogen and carbon monoxide in the syngas can be regulated to adjust the relative amounts of (i) methanol, ethanol, and $C_{3+}$ monohydric alcohol and (ii) $C_{2+}$ glycol produced by the oxygenate formation reactions (5), (9), and the homologation.

It is believed that the homologation produces $C_{3+}$ monohydric alcohol and $C_{2+}$ glycol according to the following pathways. Methanol introduced into the oxygenate formation reaction zone (or retained in the reaction zone and/or recycled to the reaction zone) is believed to react with the active material of reactions (1) and (2) via $$H[M]CO+CH_3OH\rightarrow CH_3O[M]CO+H_2, \qquad (10)$$

$$CH_3O[M]CO\rightarrow CH_3COO[M], \text{ and} \qquad (11)$$

$$CH_3COO[M]+[M']H\rightarrow CH_3COOH+[M][M']. \qquad (12)$$

Reaction (1) is then repeated, leading to $$CH_3COOH+H[M]+H[M']\rightarrow CH_3CH_2OH+H_2O+[M][M']. \qquad (13)$$

It is believed that the aldehyde is hydrogenated to produce ethanol by way of the reaction $$CH_3COH+H[M]+H[M']\rightarrow CH_3CH_2OH+[M]\{M'\}. \qquad (14)$$

At least a portion of the ethanol is separated from the products of reactions (1)-(14) for additional homologation to produce $C_{3+}$ monohydric alcohol. For example, n-propanol is believed to be produced by the reactions $$H[M]+CH_3CH_2OH\rightarrow CH_3CH_2CO[M]+H_2 \text{ and} \qquad (15)$$

$$CH_3CH_2[M]+CO\rightarrow CH_3CH_2CO[M]. \qquad (16)$$

Reaction (1) is then repeated, leading to $$CH3CH_2CO[M]+[M']H\rightarrow CH3CH2COH+[M][M']. \qquad (17)$$

The $C_3$ aldehyde is then hydrogenated to produce propanol by way of the reaction $$CH_3CH_2COH+H[M]+H[M']\rightarrow CH_3CH_2CH_2OH+[M]\{M'\}. \qquad (18)$$

If desired, a portion of the n-propanol produced in reaction (18) can be retained in the oxygenate formation reaction zone and/or or recycled to it for additional homologation, e.g., to produce butanols. While not wishing to be bound by any theory or model, it is believed that glycol homologation proceeds according to similar reaction pathways. For example, it is believed that recycled ethylene glycol reacts in the presence of the active materials produced in reactions (1) and (2) as follows:

$$H[M]CO+HOCH_2CH_2OH\rightarrow HOCH_2CH_2COO[M]+H_2 \text{ and} \qquad (19)$$

$$HOCH_2CH_2COO[M]+[M']\rightarrow HOCH_2CH_2COOH+[M][M']. \quad (20)$$

Reaction (1) is then repeated, leading to

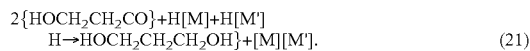

$$2\{HOCH_2CH_2CO\}+H[M]+H[M']$$
$$H\rightarrow HOCH_2CH_2CH_2OH\}+[M][M']. \quad (21)$$

If desired, all or a portion of the propylene glycol produced by reaction (21) can be retained in the oxygenate formation reaction zone and/or recycled to it for additional homologation, e.g., to produce $C_{4+}$ glycol.

The reactions (1)-(21) are typically carried out in the presence of syngas under homogeneous oxygenate formation conditions which include a temperature ≥100° C. and a pressure ≥3 Mpa (absolute). Except, e.g., for (i) light hydrocarbon (methane, ethane, etc.) as may be produced in one or more side reactions and/or (ii) gaseous diluent as may be present in the syngas, the oxygenate formation is carried out primarily in the liquid phase. Typically, the following compositions are primarily in the liquid phase during the oxygenate formation: (i) the process fluid and/or carrier fluid (including active material, active material components, and/or active material precursors that are dissolved, dispersed, suspended, or otherwise distributed therein), (ii) $C_{2+}$ glycol, particularly ethylene glycol, as may be produced in or recycled to the oxygenate formation, and (iii) $C_{2+}$ monohydric alcohol, particularly ethanol, as may be produced in or recycled to the oxygenate formation reaction zone. A composition is "primarily liquid phase" when ≥50% of the composition (weight basis) is in the liquid phase, e.g., ≥75%, such as ≥90%, or ≥95%. Typically, a reaction temperature is selected that is less than the boiling point of compositions (i), (ii), and (iii) at the reaction pressure, e.g., is at least 10° C. less, such as at least 25° C. less, or at least 50° C. less. Optionally, the oxygenate formation is carried out under conditions in which any methanol present is primarily in the liquid phase.

Typically, oxygenate formation conditions include (i) a reaction temperature in the range of from 100° C. to 400° C., e.g., 150° C. to 300° C., such as 120° C. to 250° C., or 150° C. to 220° C., and (ii) a total pressure ≥3 MPa (absolute), e.g., in the range of from 3 MPa (absolute) to 300 Mpa (absolute), such as in the range of from 6 MPa (absolute) to 30 MPa (absolute). The syngas partial pressure (the combined pressure of CO and $H_2$) is typically ≥3 MPa, e.g., in the range of from 4 MPa to 60 MPa, such as 5 MPa to 60 MPa, or 6 MPa to 30 MPa. More particularly, the carbon monoxide partial pressure can be in the range of from 3 MPa (absolute) to 100 MPa (absolute), with a total pressure in the range of from of 6 MPa to 125 Mpa.

The oxygenate formation produces a reaction mixture, at least a portion of which is conducted away from the oxygenate formation reaction zone. Typically, the reaction mixture comprises (i) an oxygenate mixture comprising ethanol and $C_{3+}$ monohydric alcohol, as produced by reactions (1)-(21); (ii) un-reacted syngas; and (iii) generally at least a portion of any remaining process fluid. Typically, little if any process fluid is withdrawn from the reaction zone. In aspects where it is desirable to withdraw or otherwise recover process fluid, the recovered process fluid can include one or more of (i) unreacted and/or reacted (e.g., spent) active material; (ii) unreacted and/or reacted active material components; and (iii) unreacted and/or reacted active material precursors. The oxygenate mixture can further comprise methanol and/or non-alcohol $C_{2+}$ oxygenate, such as ($C_2OR$) where R is not H, e.g., methyl acetate and/or ethyl acetate. Typically, the non-alcohol $C_{2+}$ oxygenate includes non-alcohol $C_{2+}$ oxygenate, e.g., non-ethanol $C_2$ oxygenate, such as ethylene glycol. The non-ethanol $C_2$ oxygenate can also include one or more of acetaldehyde, glycoaldehyde, acetic acid, hydroacetic acid, oxalic acid, glyoxalic acid, dimethyl ether, etc. These typically result from organic oxygenate-producing side reactions which occur with oxygenate formation reactions (1)-(21). The reaction mixture can further comprise the products and byproducts of other side reactions that may occur, e.g., one or more of carbon dioxide; light hydrocarbon such as methane, ethane, propane, etc.; and water and/or other non-carbnaceous inorganic oxygenate.

The reaction mixture is conducted away from the oxygenate formation reaction zone for separation and recovery of at least a portion of the reaction mixture's ethanol and $C_{3+}$ monohydric alcohol, e.g., propanols and/or butanols. It is typical to recover from the reaction mixture ≥5 wt. % of one or more of (i) the ethanol produced by the oxygenate formation, (ii) the $C_{3+}$ monohydric alcohol produced by the oxygenate formation, and (iii) the $C_{2+}$ glycol produced by the oxygenate formation, e.g., ≥10 wt. %, such as ≥25 wt. %, or ≥50 wt. %, or ≥75 wt. %, or ≥90 wt. %. It is also typical to recover from the reaction mixture ≥5 wt. % of one or more of (i) any methanol in the reaction mixture, (ii) any undispersed solids as may be present in process fluid present in the recovered reaction mixture, (iii) any carbon dioxide, (iv) any light hydrocarbon such as methane, ethane, propane, etc.; and (v) any water and/or other non-carbonaceous inorganic oxygenate; e.g., ≥10 wt. %, such as ≥25 wt. %, or ≥50 wt. %, or ≥75 wt. %, or ≥90 wt. %. Conventional separations technology can be used for the recoveries, e.g., one or more distillations, filtrations, solvent extractions, membrane separations, etc., but the invention is not limited thereto. Typically following one or more of these separations, at least a portion (e.g., ≥10 wt. %, such as ≥25 wt. %, or ≥50 wt. %) of the reaction mixture's process fluid is recycled to the oxygenate formation, optionally together with at least a portion of any active material, active material components, and/or active material precursors as may be dissolved, suspended, dispersed, or distributed therein.

At least a portion of the recovered ethanol is introduced in the liquid phase into the oxygenate formation reaction, e.g., ≥10 wt. %, such as ≥25 wt. %, or ≥50 wt. %, or ≥75 wt. %, or ≥90 wt. %. For example, substantially all of the ethanol produced in the oxygenate formation can be recovered and re-introduced in the liquid phase, e.g., as a liquid phase recycle stream. Although the recovered ethanol can remain in the liquid phase throughout the recovery and recycle, it is within the scope of the invention for the ethanol to be at least partially in the vapor phase during one or more of these operations, provided the ethanol is introduced into the oxygenate formation reaction zone primarily in the liquid phase or becomes primarily liquid phase when it is introduced into the oxygenate formation reaction zone. It is typical to recover and re-introduce into the oxygenate formation reaction zone (e.g., as a recycle stream) at least a portion of the methanol produced in the oxygenate formation reaction, such as ≥10 wt. %, or ≥25 wt. %, or ≥50 wt. %, or ≥75 wt. %, or ≥90 wt. %, or even substantially all of methanol produced by the oxygenate formation. Alternatively or in addition, methanol produced in the oxygenate formation reaction can be conducted away, e.g., for storage and/or further processing such as chemicals production. For example, recovered methanol can be converted to olefin using methods described in U.S. Patent Application Publication No. 2015/0158785A1, which is incorporated by reference herein in its entirety, and in U.S. Pat. Nos. 4,404,414; 4,665,249; 6,166,282; 7,119,240; 7,227,048; 7,879,920;

7,279,012; 7,083,762; and 7,781,633; which are incorporated by reference in their entireties. Optionally, the process includes recovering and re-introducing into the oxygenate formation reaction zone (e.g., as one or more recycle streams) at least a portion of the non-alcohol $C_{2+}$ oxygenate produced in the oxygenate formation reaction, e.g., at least a portion of the non-ethanol $C_2$ oxygenate, such as ≥10 wt. %, or ≥25 wt. %, or ≥50 wt. %, or ≥75 wt. %, or ≥90 wt. %, or even substantially all of the non-ethanol $C_2$ oxygenate produced by the oxygenate formation. For example, ≥10 wt. %, or, ≥25 wt. %, or ≥50 wt. %, or ≥75 wt. %, or ≥90 wt. %, or even substantially all of the $C_{2+}$ glycol, particular ethylene glycol, produced by the oxygenate formation can be recycled to the oxygenate formation. Alternatively or in addition, at least a portion of any recovered $C_{2+}$ glycol, particular recovered ethylene glycol, can be conducted away from the process. In certain aspects, ≥90 wt. % of the recovered $C_{2+}$ glycol is ethylene glycol, and ≥90 wt. % of the recovered $C_{3+}$ monohydric alcohol is propanols and/or butanols. Although the non-ethanol $C_{2+}$ oxygenate can be recycled to the oxygenate formation in the liquid phase, this is not required.

The specified separation, recoveries, and recycles can be carried out together or individually. For example, it is within the scope of the invention to recycle a mixture of methanol and ethanol, the recycle mixture further comprising additional recycle components, e.g. recovered ethylene glycol. Methanol and ethanol can be recovered from the process mixture (or oxygenate mixture) as a single stream, but it is more typical to recover methanol and ethanol from the reaction mixture as separate streams.

Optional Alcohol to Olefin Conversion

Certain aspects include converting to olefin, such as propylene and butylenes, at least a portion of the $C_{2+}$ monohydric alcohol, e.g., at least a portion of the $C_{3+}$ monohydric alcohol, such as at least a portion of the propanols and/or butanols. Optionally, at least a portion of any ethanol that is not used for recycle to the oxygenate formation is converted to unsaturates, such as to olefin, e.g., to one or more of ethylene, propylene, and butylenes. Polymerizing at least a portion of the olefin is also within the scope of the invention.

For example, a portion of the recovered $C_{2+}$ monohydric alcohol can be reacted in a second reaction zone (e.g., in a second stage that is located downstream of the first (oxygenate formation) stage, the second stage being configured to produce olefinic hydrocarbon and a second oxygenate. The second hydrocarbon typically comprises $C_{2+}$ olefin, e.g., one or more of ethylene, propylene, and butylenes. The second oxygenate primarily comprises water, e.g., ≥50.0 wt. % water based on the weight of the second oxygenate. The second hydrocarbon and second oxygenate can be conducted away from the second stage as components of a second reaction mixture.

In certain aspects, the second stage includes converting one or more $C_{2+}$ monohydric alcohol compounds to corresponding olefinic compounds by dehydration. In these aspects, the dehydration can be, e.g., conducted in the presence of a solid acid catalyst, such as amorphous and/or crystalline $Al_2O_3$, $ZrO_2$, and/or $WO_3$, either alone or supported on metal oxides and sulfides of W, V, Zr, and/or Mo. Polyoxometalates containing W and/or Mo are also suitable dehydration catalysts. Suitable conditions for the dehydration reaction include a temperature of at least 180° C., such as in the range of from 180° C. to 450° C. and a pressure in the range of from 0.5 atm to about 25 atm absolute (from 50 kPa to 2.5 MPa). Suitable conventional alcohol dehydrogenation processes include those described in U.S. Pat. Nos. 4,062,905; 4,079,095; 4,079,096; 3,911,041; and 4,049,573, each of which is incorporated by reference herein in its entirety.

Alternatively or in addition, the second stage includes converting one or more $C_{2+}$ monohydric alcohol compounds to corresponding olefinic compounds by least one oxygenate-to-olefin ("OTO") reaction carried out in the presence of at least one aluminophosphate molecular sieve OTO catalyst. Suitable OTO reactions include those described in U.S. Pat. Nos. 4,499,327 and 6,518,475, both of which are incorporated by reference herein in their entirety.

Conventional separation means can be utilized for separating olefins, e.g., one or more of ethylene, propylene, and butene, from the second reaction mixture, but the invention is not limited thereto. Suitable separation means are disclosed in U.S. Patent Application Publication No. 2008/0033218 A1. For example, one or more cryogenic separators can be used for separating ethylene from a mixture of propylene and butylenes. Separated olefinic compounds, e.g., one or more of separated ethylene, propylene, and butylene can be conducted away from the process, e.g., for storage or further processing, including polymerization. The separated $C_{2+}$ olefin produced by the present process can be used as feedstocks in a variety of important industrial processes, including the production of homopolymers and copolymers of ethylene, propylene, and/or butylene.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated, and are expressly within the scope of the invention. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group of consisting of," or "is" preceding the recitation of the composition, component, or components, and vice versa.

The invention claimed is:

1. A process for producing oxygenate, the process, comprising:
   (a) providing a feed mixture comprising molecular hydrogen and ≥5 wt. % of carbon monoxide;
   (b) providing a process fluid comprising at least one active material, the active material comprising at least one metal-containing compound which includes at least one of Co, Rh, Pd, Pt, Ni, Os, Ir, Cr, Mn, Fe, Re, and Ru; and wherein the process liquid further comprises:
   ($b_1$) at least one anionic compound comprising phosphorus and/or nitrogen and (b$_2$) at least one anionic compound comprising halogen (c) producing a reaction mixture by reacting at least a portion of the feed mixture's CO and at least a portion of the feed mixture's molecular hydrogen in the presence of the process fluid under oxygenate formation conditions, wherein
  (i) the reaction mixture comprises oxygenate produced by the reaction and at least a portion of any un-reacted feed mixture, and
  (ii) the oxygenate comprises C$_{2+}$ glycol, ethanol, and C$_{3+}$ monohydric alcohol;

(d) separating from the reaction mixture (i) at least a portion of the ethanol, (ii) at least a portion of the C$_{3+}$ monohydric alcohol, and (iii) at least a portion of the C$_{2+}$ glycol;

(e) recycling to the reaction at least a liquid-phase portion of the separated ethanol; and (f) conducting away at least a portion of the separated C$_{3+}$ monohydric alcohol and at least a portion of the separated C$_{2+}$ glycol.

2. The process of claim 1, wherein ≥10 wt. % of the reaction mixture's ethanol is recycled in step (e).

3. The process of claim 1, further comprising recycling to the reaction 10 wt. % to 90 wt. % of the separated C$_{2+}$ glycol, and wherein ≥90 wt. % of the separated C$_{2+}$ glycol that is not recycled is conducted away.

4. The process of claim 1, further comprising recycling to the reaction 1 wt. % to 10 wt. % of the separated C$_{3+}$ monohydric alcohol, and wherein ≥90 wt. % of the separated C$_{3+}$ monohydric alcohol that is not recycled is conducted away.

5. The process of claim 1, wherein the reaction mixture's oxygenate further comprises methanol, the process further comprising recycling ≥10 wt. of the reaction mixture's methanol.

6. The process of claim 1, wherein the reaction of step (c) is carried out primarily in the liquid phase.

7. The process of claim 1, wherein the oxygenate formation conditions include a CO partial pressure in the range of from 3 MPa to 100 MPa, a total pressure in the range of from of 6 MPa to 125 Mpa, a temperature of 100° C. to 400° C., and the temperature is less than ethanol's boiling point at the total pressure.

8. The process of claim 1, wherein the feed has an H$_2$: CO molar ratio in the range of from 0.01 to 10.

9. The process of claim 1, wherein the process fluid further comprises liquid oxygenate and at least one promoter.

10. The process of claim 1, wherein the metal-containing compound includes at least one of Co, Rh, Re, Ir, and Ru.

11. An oxygenate homologation process, the process, comprising:
  (a) providing a primarily vapor-phase feed mixture comprising molecular hydrogen, ≥5 wt. % of carbon monoxide;
  (b) providing a process fluid comprising (i) methanol and primarily liquid-phase C$_{2+}$ organic oxygenate and (ii) at least one active material, the active material comprising at least one metal-containing compound which includes at least one of Co, Rh, Pd, Pt, Ni, Os, Ir, Cr, Mn, Fe, Re, and Ru; and wherein the process liquid further comprises:
  (b$_1$) at least one anionic compound comprising phosphorus and/or nitrogen and
  (b$_2$) at least one anionic compound comprising halogen
  (c) reacting at least a portion of the feed mixture's CO and at least a portion of the feed mixture's molecular hydrogen in the presence of the process fluid under homologation conditions, wherein the reaction mixture comprises:
    (i) homologated organic oxygenate produced by one or more homologations of at least a portion of the process fluid's organic oxygenate, the homologated organic oxygenate comprising ethanol, C$_{3+}$ monohydric alcohol, and C$_{2+}$ glycol, and
    (ii) at least a portion of any un-reacted feed mixture;
  (d) separating from the reaction mixture (i) at least a portion of the ethanol, wherein the organic oxygenate of step (b) includes at least a portion of the separated ethanol in the liquid phase, (ii) at least a portion of the C$_{3+}$ monohydric alcohol, and (iii) at least a portion of the C$_{2+}$ glycol; and
  (e) conducting away at least a portion of the separated C$_{3+}$ monohydric alcohol and at least a portion of the separated C$_{2+}$ glycol.

12. The process of claim 11, wherein the organic oxygenate of step (b) includes ≥10 wt. % of the reaction mixture's ethanol.

13. The process of claim 11, wherein the organic oxygenate of step (b) includes 10 wt. % to 90 wt. % of the separated C$_{2+}$ glycol.

14. The process of claim 11, wherein the organic oxygenate of step (b) includes 1 wt. % to 10 wt. % of the separated C$_{3+}$ monohydric alcohol.

15. The process of claim 11, wherein the process further comprises recycling ≥10 wt. of any methanol in the reaction mixture.

16. The process of claim 11, wherein the feed has an H$_2$: CO molar ratio in the range of from 0.01 to 10.

17. The process of claim 11, wherein the metal-containing compound includes at least one of Co, Rh, Re, and Ru.

18. The process of claim 11, wherein the temperature in step (c) is less than ethanol's boiling point at the total pressure.

19. The process of claim 17, wherein the homologation conditions include a CO partial pressure in the range of from 3 MPa to 100 MPa, and a total pressure in the range of from of 3 MPa to 300 Mpa, and a temperature of 100° C. to 400° C.

20. An oxygenate production process comprising:
  (a) providing a feed mixture comprising molecular hydrogen, ≥5 wt. % of carbon monoxide;
  (b) providing a process fluid comprising organic oxygenate and (ii) at least one active material; the active material comprising at least one metal-containing compound which includes at least one of Co, Rh, Pd, Pt, Ni, Os, Ir, Cr, Mn, Fe, Re, and Ru; and wherein the process liquid further comprises:
  (b$_1$) at least one anionic compound comprising phosphorus and/or nitrogen and
  (b$_2$) at least one anionic compound comprising halogen
  (c) reacting at least a portion of the feed mixture's CO and at least a portion of the feed mixture's molecular hydrogen in the presence of the process fluid under oxygenate formation conditions to produce ethanol, C$_{3+}$ monohydric alcohol, and non-alcohol C$_{2+}$ oxygenate;
  (d) recycling to the reaction of step (c) at least a portion of the non-alcohol C$_{2+}$ oxygenate; and
  (e) conducting away at least a portion of the C$_{3+}$ monohydric alcohol.

21. An oxygenate production process, comprising:
  (a) providing a feed mixture comprising molecular hydrogen, ≥5 wt. % of carbon monoxide;

(b) providing a process fluid comprising at least one active material, the active material comprising at least one metal-containing compound which includes at least one of Co, Rh, Pd, Pt, Ni, Os, Ir, Cr, Mn, Fe, Re, and Ru; and wherein the process liquid further comprises:

($b_1$) at least one anionic compound comprising phosphorus and/or nitrogen and ($b_2$) at least one anionic compound comprising halogen (c) producing an oxygenate mixture by reacting at least a portion of the feed mixture's CO and at least a portion of the feed mixture's molecular hydrogen in the presence of the process fluid under oxygenate formation conditions, wherein the oxygenate mixture comprises $C_2$ oxygenate and $C_{3+}$ oxygenate;

(d) removing an extract from the oxygenate mixture to produce a raffinate, wherein the extract comprises ≥10 wt. % of the oxygenate mixture's $C_2$ oxygenate;

(e) introducing a liquid-phase portion of the extract into the reaction; and (f) removing at least a portion of the $C_{3+}$ oxygenate produced in step (c) from the oxygenate mixture and/or the raffinate.

22. The process of claim 20, wherein the oxygenate formation conditions include a total pressure in the range of from of 3 MPa to 300 Mpa, a temperature ≥100° C., and the temperature is less than ethanol's boiling point at the total pressure.

23. The process of claim 20, wherein the feed has an $H_2$:CO molar ratio in the range of from 0.01 to 10.

24. The process of claim 20, wherein the metal-containing compound includes carbonyl of at least one of Co, Rh, Ir, Re, and Ru.

25. The process of claim 20, further comprising separating at least a portion of any ethylene glycol from the non-ethanol $C_2$ oxygenate before recycling the non-ethanol $C_2$ oxygenate to the reaction of step (c).

26. The process of claim 25, further comprising recycling at least a portion of the ethanol to the reaction of step (c).

27. The process of claim 20, wherein the (i) $C_{3+}$ monohydric alcohol includes propanol and (ii) the ethanol and propanol are produced in step (c) at an ethanol: propanol molar ratio ≤10.

28. The process of claim 21, wherein the removed $C_{3+}$ oxygenate includes propanol.

29. The process of claim 20, wherein the recycled portion of the portion of the non-alcohol $C_{2+}$ oxygenate includes non-ethanol $C_2$ oxygenate.

* * * * *